(12) United States Patent
Kirkegaard et al.

(10) Patent No.: US 7,344,893 B2
(45) Date of Patent: Mar. 18, 2008

(54) IMMUNO-GOLD LATERAL FLOW ASSAY

(75) Inventors: Leslie Kirkegaard, Ijamsville, MD (US); Glen Ford, Montgomery Village, MD (US)

(73) Assignee: Auric Enterprises, LLC, Jackson, WY (US)

( * ) Notice: Subject to any disclaimer, the term of this patent is extended or adjusted under 35 U.S.C. 154(b) by 0 days.

(21) Appl. No.: 11/248,214

(22) Filed: Oct. 13, 2005

(65) Prior Publication Data
US 2007/0087450 A1    Apr. 19, 2007

(51) Int. Cl.
G01N 33/53    (2006.01)
(52) U.S. Cl. .................. 436/514; 435/7.1; 435/7.2; 435/7.94; 435/287.1; 435/287.2; 435/288.1; 435/288.2; 435/970; 436/518; 436/810; 436/814
(58) Field of Classification Search ................ 435/7.1, 435/7.2, 7.94, 287.1–288.2, 970; 422/55–62; 436/514, 518, 810, 814
See application file for complete search history.

(56) References Cited

U.S. PATENT DOCUMENTS

| 4,094,647 | A  |  6/1978 | Deutsch et al. |
| 4,235,601 | A  | 11/1980 | Deutsch et al. |
| 4,361,537 | A  | 11/1982 | Deutsch et al. |
| 4,366,241 | A  | 12/1982 | Tom et al. |
| 5,120,643 | A  |  6/1992 | Ching et al. |
| 5,418,171 | A  |  5/1995 | Kimura et al. |
| 5,622,871 | A  |  4/1997 | May et al. |
| 5,656,503 | A  |  8/1997 | May et al. |
| 6,277,650 | B1 |  8/2001 | Nazareth et al. |
| 6,352,862 | B1 |  3/2002 | Davis et al. |
| 6,824,997 | B1 | 11/2004 | Moore et al. |
| 6,841,159 | B2 |  1/2005 | Simonson |
| 2001/0039057 | A1* | 11/2001 | Douglas et al. ............. 436/169 |

FOREIGN PATENT DOCUMENTS

WO    WO 94/12879    *  6/1994

* cited by examiner

Primary Examiner—Bao-Thuy L. Nguyen
(74) Attorney, Agent, or Firm—John M. Naber; Eggerton Campbell; Dickinson Wright PLLC

(57) ABSTRACT

A chromatographic lateral-flow assay system for rapid, high sensitivity method of detecting low levels of ligands in body fluids, with few false positives and few false negatives. The lateral-flow assay may have a membrane strip in ribbon form, which increases detection on the order of 2 to 10 fold over the conventional chromatographic specific binding assay techniques by placing a dried or lyophilized conjugate in colloidal spheres opposite side of the lateral flow membrane strip. A chromatographic specific binding assay strip device, comprising: a laminate strip having a first side and an opposite second side; a conjugate pad or membrane disposed on said first side of said laminate; a sample receiving pad or membrane strip and reservoir pad or membrane disposed on said second side of said laminate; and a detection pad or membrane strip disposed between the sample pad or membrane and the reservoir pad or membrane on said second side of said laminate. The assay system comprises a housing device, such as a test tube or cassettes to facilitate the mixing of a sample solution with the dried or lyophilized conjugate, and kits.

13 Claims, 3 Drawing Sheets

IMMUNO-GOLD LATERAL FLOW ASSAY

FIELD OF THE INVENTION

The present invention generally relates to an assay system and apparatus involving specific binding of analytes and/or ligands, and specifically relates to chromatographic flow binding assays with a colored conjugate, and a novel lateral-flow-platform that includes a dried or lyophilized colloidal sphere conjugate, such as gold, to the back of the lateral flow test.

BACKGROUND OF THE INVENTION

It is increasingly desirable to provide a rapid high sensitivity system to detect low levels of ligands in body fluids, plant extracts, environmental samples, tissue samples and enrichment broths. Ideally, such systems should have a minimal number of procedural steps and yield reliable results, even when used by untrained persons. A ligand may be a specific sequence of amino acids or molecule found on proteins such as an antibody, protein receptors, bacterial/microbial peptides, hormone, or drug that binds to a receptor. A receptor is any of various specific protein molecules in surface membranes of cells and organelles to which complementary molecules, such as hormones, neurotransmitters, antigens, or antibodies, may become bound. The ligand may also be a chemical intermediate or reactant with an analyte. Analytes are substances that bind to a ligand. Ligands or analytes may also be peptides, drugs, carbohydrates, haptens, chemicals, chemical reaction with an intermediate compound, and the like.

To a significant extent, many known tests presently available for detecting ligands are either time consuming, labor intensive, or in need of instrumental assistance to read results. Most known tests also lack an acceptable degree of sensitivity or specificity. This is unfortunate since rapid testing is important for diagnosis and treatment of various physiological conditions; detection of certain strains of micro-organisms; determination of the most appropriate antibiotic treatment of a patient; detection of drug analytes in individuals; detection of cancer cells in a patient's bio-fluid; detection of antibody to a microbial agent; detection of a disease-state protein; and the like.

Although known types of ligand-receptor assays have been used to detect the presence of various substances, such as ligands, there is a need in the art to provide a rapid, high sensitivity assay requiring a minimum degree of skill from a user. Rapid test assay devices for field use, such as in a home or doctor's office are known in the art for detecting proteins, peptides, drugs, carbohydrates, haptens, chemicals, chemical reaction with intermediate compounds, and the like. Such devices are referred to as one-step lateral flow or one-step immuno-chromatographic assays. These types of assay devices require a minimal number of steps and can be performed by an untrained person. Examples of these test devices abound, and the individual components of a typical one-step lateral flow test are described below:

A first type of test device involves a test strip of rectangular or square dimensions made of a vinyl, polypropylene, or other pliable or non-pliable plastic laminate to serve as a backing to hold in place other test components that are on an adhesive bond on the backing. A ligand, protein or analyte binding membrane having discreet zones of immuno-reactive proteins or substances immobilized or attached, are usually in linear impregnation or spotted through a dropper onto the membrane. The membrane may be composed of nylon, nitrocellulose, mixed cellulose esters, polysulfones, and the like. If the assay is used to detect an animal antibody, the immuno-reactive protein coated on the membrane may be a ligand to which antibody contained in a positive sample reacts. These immuno-reactive proteins used to coat the membrane are typically native or recombinant proteins derived from Human Immunodeficiency Virus (HIV), human T-cell lymphotropic viruses (HTLV), *Mycobacterium tuberculosis* (TB), and the like. In a second construct, the membrane may also be impregnated with anti-antibody to capture total class and subclass immunoglobulins. In this case, the specific antibody in the sample may react with native or recombinant ligand proteins, such as HIV, HTLV, or TB, coated onto the surface of the conjugate particles. A third construct may have native or recombinant protein antigens coated on both conjugate and membrane surfaces that react with separate binding domains on the antibody. If the membrane is detecting antigen as the analyte, the surface may be impregnated with antibody or ligand reactive with the antigen. Constructs one, two and three are known as "sandwich" type rapid assays, since the analyte being detected is captured (sandwiched in between) by both the immuno-conjugate and the membrane surface. A fourth method is a competitive inhibition assay, wherein sample analyte at detectable levels either saturates the anti-analyte conjugate or saturates the immobilized anti-analyte capture line on the membrane resulting in no visible line formation. A negative reaction in this case results in a visible line formation, due to the binding of the conjugate with the test line.

A second group of test devices involve a fibrous membrane, such as, for example, glass, polyester, cotton, or spun polyethylene, in contact with a membrane containing ligand and bound to densely colored particles such as latex, gold, silver, selenium, carbon, and the like. The bound ligand is complementary to the assay being constructed and reacts with the analyte being detected. The coated colored particles are often described as an immuno-conjugate. Sufficient molecules of ligand are coated onto the surface of the colored particles so that when a positive reaction does occur the discreet, striped, or spotted zones on the membrane surface are visible to the naked eye. A sample negative for the ligand being detected may leave a white zone in a sandwich type immuno-assay. If the assay is a competitive inhibition type, a negative sample yields a visible line or spot. The colored particles may be dried down onto the fibrous pad or membrane and placed at the dorsal end (at the opposite end of the absorbent pad or membrane) of the membrane. Release agents may be contained in the dried down colored particles to facilitate re-hydration of the particles, allowing them to react with the analyte being detected.

A third group of test devices include a fibrous sample receiving pad or membrane, such as glass, polyester, cotton, or spun polyethylene, that is partially in contact with the immuno-conjugate and serves as a reservoir for absorbing and releasing sample. The sample may contain chemicals to facilitate reactive qualities of the assay. The sample may be any biological fluid (bio-fluid) such as tissue extracts, blood, serum, plasma, tears, perspiration, urine, or saliva. The sample may also be derived from an environmental extract, plant extract, or microbial enrichment broth. When a sample or diluted sample is applied to the sample receiving pad or membrane, the movement of liquid is chromatographic and unidirectional towards the absorbent pad or membrane. During migration, the sample re-hydrates the colored particles and reacts with ligand bound to the particles.

Other test devices are known. For example, one has a bulbous absorbent pad or membrane, which serves as a reservoir for absorbing all liquid components that pass through the membrane. The absorbent material is typically cotton or paper. Another has a zone applied to the membrane containing a control line indicating sample was applied, or that the assay's immuno-conjugate is functional. The control can react with the sample or conjugate. Still another has buffered diluent often used to dilute and condition the sample being detected, allowing for exotic chemistries to occur, thus improving assay performance. The diluent is composed of salt solutions, detergents, and the like and may be applied from a dropper tip, vials, or is contained in a sample vial. And finally another has a plastic or cardboard housing to contain, provide support, and allow ease of use for the whole strip.

It is important to note that in the known prior art the conjugate pad or membrane is in the same plane as the membrane, and overlaps, or is in constant contact with the membrane. Further, the conjugate is in dry form disposed or deposited in the flow path upstream of the test site. This gives rise to a very specific flow path wherein the sample re-hydrates the dried conjugate and travels through the absorbent pad or membrane. The flow path is known as an absorbent flow path since the liquid sample is absorbed by the sample receiving pad or membrane, and next wets the conjugate pad or membrane. Typically, the amount of sample required to wet the conjugate pad or membrane is about 10 to 20 microliters (µl). The sample and conjugate mixture subsequently travels through the conjugate pad or membrane, then contacts the membrane and flows onto the test (flow) membrane.

In use, in most lateral flow assays using antigen-antibody reactions, the immuno conjugate is composed of synthetic conjugates having latex microparticles, enzymatic, fluorescent, or visually observable metal sol tags. In all these assays, there is a receptor, for example an antibody, which is specific for the selected ligand or antigen, a means for detecting the presence, and often a quantity of the ligand-receptor reaction product. Examples of such qualitative assays include blood typing and most types of urinalysis. For these semi-quantitative type positive/negative tests, visually observable indicia such, as the presence of agglutination or a color change are preferred.

Positive/negative assays (or semi-quantitative) must still be very sensitive because of the often small concentrations of the ligands of interest in the test fluid. False positives may be troublesome, particularly with agglutination and other rapid detection methods such as dipstick and color change tests. Because of these problems, sandwich and competitive inhibition assays and other detection methods that use metal sols or other types of colored particles have been developed in an attempt to increase sensitivity of detection. In addition, the use of direct labels attached to one of the specific binding ligands produces instant analytical results without the need to add further reagents. Nevertheless, these techniques have not solved all problems related to sensitivity, neither have they been reliable in obtaining results with a minimal number of method steps encountered in these rapid detection methods.

Various other techniques have been devised for labeling one member of a specific binding pair so that the binding reaction may be indirectly observed. The results of specific binding reactions are generally not directly observable. Useful labels include radiolabels, chromophores, fluorophores, (the presence of which may be detected by means of radiation detectors), spectrophotometers, the naked eye, and the like. Where members of a specific binding pair are tagged with an enzyme label, their presence may be detected by the enzymatic activation of a reaction system including a signal generating a substrate/cofactor group wherein a compound, such as a dye, is activated to produce a detectable signal.

Other specific binding assay devices are known in the art having vertically arranged elements including the following: a porous capture material impregnated at a reaction site with a member of a specific binding pair such as an antibody or an antigen; a removable prefilter disposed above the capture material; and, a blotter disposed below the capture material. A sample liquid such as blood, serum or other bio-fluid is added to the device wherein the prefilter removes particulates and other impurities from the sample. These impurities would otherwise be trapped on top of the specific binding capture material. Analyte substances within the sample are trapped by means of specific binding reactions with their specific binding partners on the capture material. Non-analyte components of the sample solution pass through the capture material and are absorbed by the blotter. Wash steps may be carried out to remove non-analyte components from the capture material and additional reagents such as enzyme substrates, cofactors and dye precursors may be added to the capture material to indicate the presence or absence of analyte at the reaction site. The prefilter should then be removed so that the presence or absence of analyte at the reaction site may be visually determined. Unfortunately, while these devices are somewhat useful, they suffer from limitations in capture efficiency and sensitivity because most of the analyte in the sample 10 material flows around, rather than through, the reaction site on the capture material.

Several one-step lateral flow immunoassay devices, having a strip capable of transporting a developing liquid by capillary action having a first zone for receiving a sample, a second zone impregnated with a first reagent capable of being transported by the developing liquid, and a third zone impregnated with a second reagent, are known in the art (See generally, U.S. Pat. Nos. 4,366,241; 4,094,647; 4,235,601; 4,361,537; and 6,841,159). U.S. Pat. Nos. 6,352,862; 5,622,871; and 5,120,643 also relate to one-step lateral flow tests wherein the conjugate is in dry form along the flow path.

A major disadvantage of all of the known prior art is that the sample rehydrates the dried conjugate along the flow path. Thus, the majority of sample applied is not involved in the immunological reaction. For example, between 10 µl to 20 µl of sample is all that is required to fully rehydrate a 5 by 5 mm gold pad or membrane with the conjugate pad or membrane composed of polyester, glass, nylon, cellulose or other fibers. Since the conjugate pad or membrane is in the device flow path and in contact with the membrane, a minimal remaining sample is involved in the immunological reaction. The remaining 50 µl to 150 µl of sample acts as a liquid front by pushing the reacted analyte conjugate complexes through the flow path. Thus, a severe limitation of the one-step lateral flow assay is the limited amount of sample actually involved in the reaction with the conjugate. None of the known prior art teach or suggest locating the conjugate pad or membrane on the reverse side of the strip, and not in contact with either the sample receiving pad or the membrane. By locating the conjugate pad or membrane on the reverse side of the membrane, the entire sample first rehydrates the conjugate resulting in a uniform dispersion of conjugate through the entire applied sample. Further, in a one-step lateral flow assay, as a sample mixes with a dry conjugate, incomplete mixing often yields conjugate particles with vastly different numbers of captured analyte molecules. This alone may be a source of decreased sensitivity since the maximum number of analyte molecules are not captured on the surface of the conjugate particles.

Other designs are known in the art also include two-step assays. These often require the conjugate pad or membrane to be physically and spacially removed from the test strip. For example, there are assays known in the art where the conjugate is contained in book form, or a "male to female" molded apparatus. In the book form, the test strip is located on one panel of the book while the conjugate is located on the other panel. The test requires the user to close both halves for the test to begin. With the "male to female" apparatus, the sample is applied to the male portion of the apparatus, and the two halves are closed to initiate the reaction. Another format has the conjugate dried and located on a separate sampling stick. The sampling stick is mixed with a sample and is then fixed in the cassette sample well. For example, some two step assay platforms are known in the art, such as indicated in U.S. Pat. No. 6,824,997 and U.S. Pat. No. 5,418,171. These tests have a significant drawback though. The end user must perform an additional step to physically bring the membrane and conjugate into contact after the sample has been adequately mixed.

Thus, there is a desire and need in the art for a high sensitivity assay system and apparatus to rapidly detect low levels of ligands in a small sample size of fluid. Such new tests should involve a minimal number of procedural steps while at the same time, yielding reliable results, even when used by untrained persons. Such a system and apparatus would be useful in areas of infectious disease, pregnancy, microbial detection, ovulation, cancer marker identification, autoimmunity, cardiac markers, biowarfare agents, allergy, drugs of abuse and environmental monitoring, and the like.

SUMMARY OF THE INVENTION

The present invention generally relates to a rapid high sensitivity system apparatus and method for detecting low levels of ligands in body bio-fluids, environmental and tissue culture extracts, with high sensitivity and specificity.

The invention includes a system and method for a semi-qualitative (e.g., positive/negative) indicator, such as the presence of agglutination or a color change, as well as quantitative determination. Accordingly, it is an important aspect of one embodiment of the present invention to provide a system and method of analyte detection having a membrane strip that increases detection on the order of 2 to 10 fold over the conventional chromatographic specific binding assay techniques by placing a dried or lyophilized colloidal sphere conjugate to the back of a lateral flow test. Preferably gold colloidal spheres are used, but other metal sols and latex microparticles may be used as well.

Another important aspect of the invention is the inclusion of a novel conjugate pad or membrane solution dried onto the conjugate pad or membrane. This solution is composed of negatively charged detergents that are coated onto the conjugate pad or membrane. When sample contacts a conjugate pad or membrane, the labeled colored particles are rapidly expressed into the sample where the test ligand has an increased opportunity to react with said conjugate particles.

Other important aspects of the present invention may include several cassettes for use with the test strip. The cassettes are designed to allow for sample loading either on the reverse of the cassette, the cassette side, or on the front of the cassette. When loading the sample on the front or side of the cassette, the cassette contains ridges or channels designed both to transport the sample directly to the conjugate pad or membrane and to pre-mix the sample and conjugate.

Additional aspects and advantages of the invention will become apparent from the following detailed description, the drawings, and the appended claims.

BRIEF DESCRIPTION OF THE FIGURES

The foregoing features, as well as other features, will become apparent with reference to the description and figures below, in which like numerals represent like elements, and in which.

DETAILED DESCRIPTION OF THE INVENTION

The present invention generally relates to a rapid, high sensitivity chromatographic assay for detecting low levels of ligands in bio-fluids, environment, plant and tissue culture extracts, using a minimal number of procedural steps even when used by untrained persons. The present invention encompasses diagnostic kits that may contain a chromatographic specific binding assay system, and preferably an immunochromatographic specific binding assay system. Furthermore, the system and apparatus, because of its accuracy and simple method steps, make it appropriate for field use such as a home, clinic, point of care setting, or doctor's office. Test results may be visually read or read by an instrument known in the art and readily available to give either a semi-qualitative (e.g., a positive/negative result) or a quantitative result. In use, the present invention is simple to use and requires a minimum degree of user skill and involvement.

Figure 2:
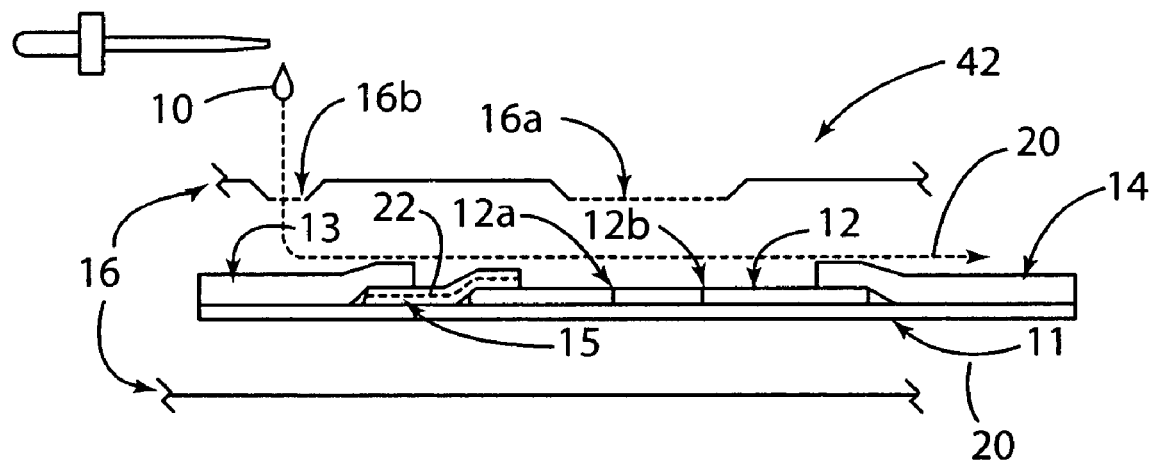
FIG. 2 is an expanded side view of prior art chromatographic elements assembled into a test device.

To assist in understanding the present invention, FIG. 2 illustrates a side view of an expanded prior art assay platform device having chromatographic elements and is generally indicated at 42. The main components of device 42 are a sample receiving pad or membrane 13 composed of a fibrous membrane such as cotton, glass fibers, polyster, nitrocellulose or nylon (where the sample fluid 10 is initially applied) and a cassette 16 shown in expandable halves and a laminate 11. A liquid sample 10 is applied through holes (cassette 16 openings) 16b onto a sample receiving pad or membrane 13. The sample fluid 10 flows out of the sample receiving pad or membrane 13 toward an adjacent dried or lyophilized mobile conjugate pad 15 and is along a flow path 20, composed of a fibrous membrane, where the sample 10 and mobile conjugate 22 has an opportunity to mix and flow through capillary migration into an elongated lateral flow analyte detection fibrous membrane strip 12 toward the direction of reservoir pad or membrane 14, located at the opposite end of the sample receiving pad or membrane 13 conjugate. Sample 10 and conjugate mixture 22 then continue to migrate to an immobilized capture reagent membrane at region 12a of detection membrane strip 12, where the sample/conjugate mixture can bind or stick to the immobilized capture reagent, causing a color reaction, indicating the presence of a specific ligand or analyte. The presence and/or amount of analyte in the sample 10 may be determined by the visibility of a line formed by the capture reagent 12a, specific for the analyte-label reagent conjugate being tested. Detection may be observed through a viewing window area 16a of cassette 16 having a transparent cover. There is also a control reagent region 12b, which is used to verify that the reagents are reacting as they should. The membrane strips or pads are attached to laminate 11 (semi-rigid) to maintain its elongated structure. A cassette case 16 is also used to maintain rigidity and prevent contamination of fluids that may alter the capillary flow of the foreign fluids toward the reservoir pad or membrane 14. Membrane 14 is typically composed of cotton, paper or glass fiber. Membrane 12 regions may be composed of nitrocellulose, mixed cellulose ester, nylon and the like. A major shortcoming of all of the known prior art is that sample 10 rehydrates the dried conjugate 22 along the flow path 20 at the conjugate pad or membrane 15, starting from the sample application area 16b, flowing in the direction of the reservoir absorbent pad as shown at 20 in FIG. 2. Thus, the majority of sample 10 applied is not involved in the immunological reaction. In fact, most of the sample 10 acts as a liquid front, pushing the reacted analyte conjugate complexes through flow path 20 and is actually not involved in the reaction with the conjugate 22.

Figure 1:
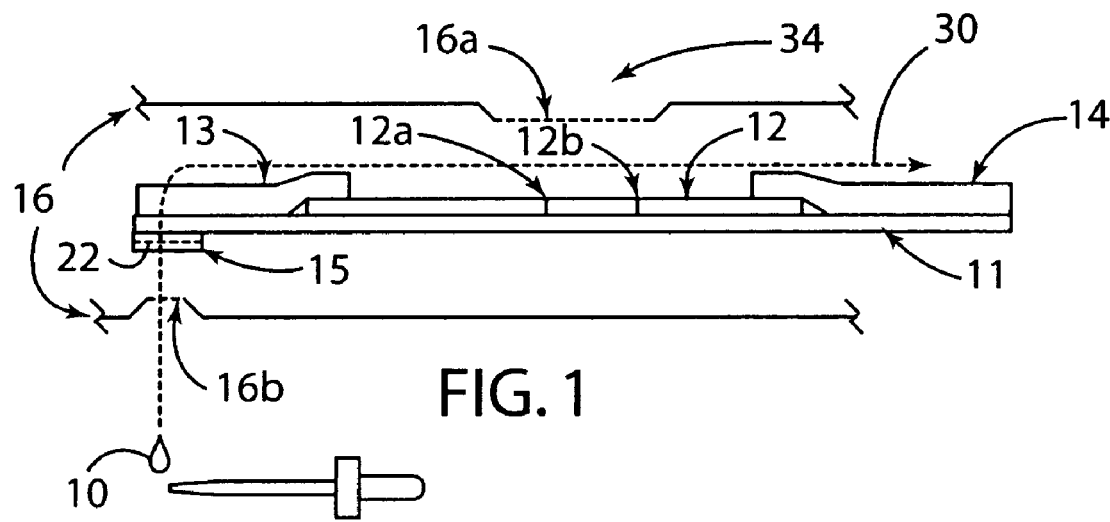
FIG. 1 is an expanded side view of chromatographic elements assembled into a test device in accordance with the objects' present invention.

FIG. 1 illustrates a possible embodiment of the present invention assay platform device and is generally indicated at 34. Device 34 is shown in expanded side view to illustrate the individual component configuration of the chromatographic elements. Noted differences over the prior art are the change in location of cassette opening (sample well) 16b to the underside of cassette 16 and its immediate contact with conjugate pad or membrane 15. Device 34 may be configured to perform at least four types of assays including: secondary antibody sandwich for measurement of sample antibody; antibody-antigen-antibody sandwich for measurement of antigen in either competitive (inhibition) or non-competitive mode; antigen-antibody-antigen sandwich for measurement of antibody; and competitive inhibition assay involving antigen bound to the conjugate microparticles, anti-antigen on the membrane, with detectable analyte inhibiting the anti-antigen reaction.

Figure 3A:
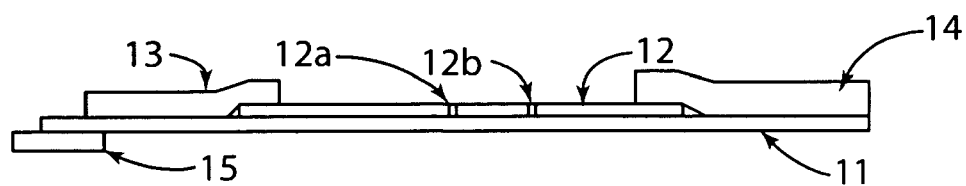
FIGS. 3a-3c are side views of chromatographic elements assembled into a test device with alternative layouts of the conjugate pad or membrane in accordance with the objects' present invention.
Figure 3B:
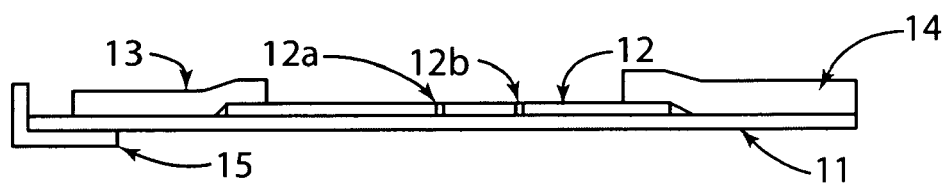
Figure 3C:
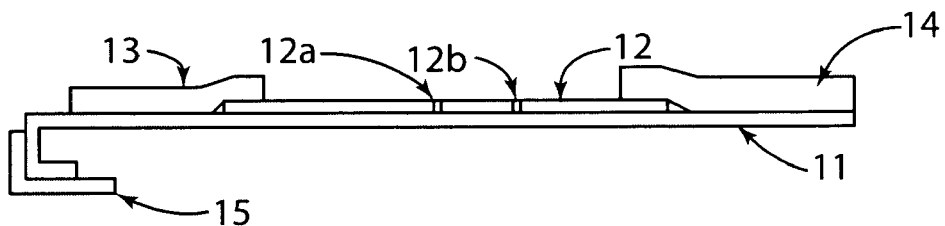

In the proposed immunoassay device of the present invention, the dried or lyophilized conjugate pad or membrane 15 may contain metal sols, enzymatic, fluorescent, latex microparticles, and the like, preferable colloidal gold particles. Conjugate pad or membrane 15 is attached to the side of laminate or semi-rigid material 11, opposite sample receiving pad or membrane 13. The entire elongated assay strip and components are enclosed in a plastic cassette 16. Liquid sample 10 is applied to holes or openings 16b directly unto the conjugate pad or membrane 15, allowing a complete mixing of the conjugate particles 22 with sample fluid 10. The completely mixed sample 10 and conjugate 22 next flows by gravity and/or capillary action around laminate 11 (as shown in FIG. 3) onto sample receiving pad or membrane 13 along flow path 30. This allows sample fluid 10 to rehydrate conjugate particles 22, creating a more complete mixture of sample 10 and conjugate 22 compared to the application methods in the prior art. Sample 10 and mobile conjugate mixture next flows through capillary migration into the elongated lateral flow analyte detection fibrous membrane strip 12 along flow path 30 (toward the reservoir pad or membrane 14, located at the opposite end of the sample receiving pad or membrane 13). Sample 10 and conjugate 22 mixture then continues to migrate to an immobilized capture reagent membrane region 12a, where the sample/conjugate mixture can bind or stick to the capture reagent, causing a color reaction, indicating the presence of a specific ligand or analyte. The presence and/or amount of analyte in the sample 10 may be determined by the visibility of a line formed by the capture reagent 12a, specific for the analyte-label reagent conjugate, which is detected in the viewing window area 16a which may be a transparent cover over an opening in the cassette cover 16 and known in the art. There is also a control reagent feature 12b, which is used to verify that the reagents are reacting as they should. The major advantage of the present invention over the prior art is the flow path 30 may now be one in which the liquid phase containing sample 10 and conjugate 22 is first pre-mixed prior to contacting sample receiving pad or membrane 13. The dried or lyophilized conjugate 22 in the conjugate membrane 15 may consist of latex microparticles, enzymatic, fluorescent, or visually observable tags such as silver, selenium, carbon, other metal sol tags, preferable colloidal gold spheres. The detection membrane strip 12, sample receiving pad or membrane 13, conjugate pad or membrane 15, or reservoir pad or membrane 14 may be composed of a series of porous material pieces such as, paper, cotton, polyester, glass, nylon, mixed cellulose esters, spun polyethylene, polysulfones, and the like. Preferably, nitrocellulose, nylon or mixed cellulose esters are used for the analyte detection membrane strip 12, while paper, cotton, polyester, glass fiber or polyethylene are preferred for the conjugate pad 15, sample receiving pad or membrane 13 and reservoir absorbent 14.

Figure 4:
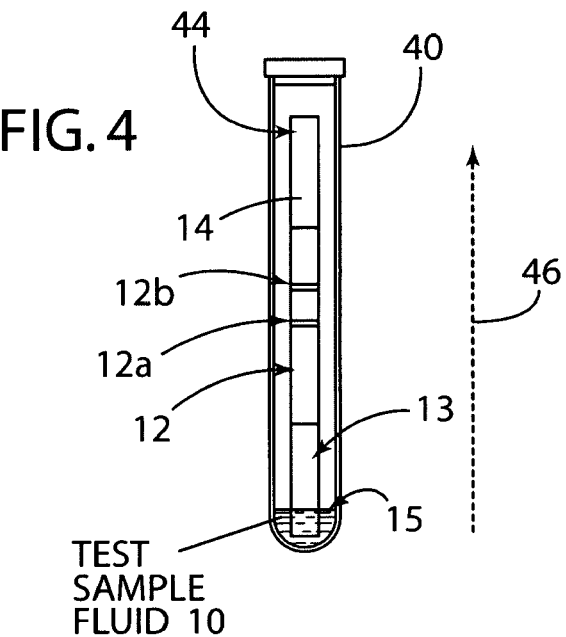
FIG. 4 is a perspective view of a chromatographic assay device enclosed in a chamber in accordance with the objects' present invention.

In a test tube 40 version of the assay illustrated at FIG. 4 conjugate pad or membrane 15 and sample 10 are mixed prior to contact with the sample receiving pad or membrane 13 and flows along a path 46. Thus, in both the test tube 40 version and cassette 16 version the flow path is one in which sample 10 and conjugate 22 go through a liquid, non-absorbent phase prior to being absorbed onto a sample receiving pad or membrane 13.

In one embodiment of the present invention the detection membrane 12 and sample receiving pad or membrane 13 and conjugate pad or membrane 15 may optionally contain blocked bovine serum albumin (BSA) and detergent to prevent loss of human antibody, by non-specific attachment.

A reservoir pad or membrane 14 at the distal end of the device receives and absorbs liquid sample 10 and conjugate 22 material to facilitate capillary migration through the detection membrane 12 along the pre-configured flow path. A buffered diluent may be used to dilute and condition sample 10 being detected, allowing for binding and/or chemical reactions to occur to improve assay performance. The diluent may be composed of salt solutions, detergents, and the like and may be applied from a dropper tip vials or contained in a sample vial. A capture ligand 12a is attached to the detection membrane 12, and a second region 12b performs a built in control feature.

The whole strip should be contained in a plastic or cardboard housing (cassette 16) to provide support and for ease of use. The cassette 16 may contain ridges designed to both mix the sample 10 and conjugate 22 and to facilitate eventual contact with the sample receiving pad or membrane 13. The cassette may have ridges or channels to facilitate (channeling) of sample 10 to contact the conjugate pad or membrane 15.

FIGS. 3(a-c) illustrate alternative embodiments of the present invention wherein the chromatographic elements assembled into an assay platform device. The location of the conjugate pad or membrane 15 is varied as is the shape of laminate 11 to illustrate different placement locations of the dried or lyophilized mobile conjugate pad or membrane 15. These variations illustrate a key technical advantage of the present invention over the prior art in that it is not dependant upon the exact placement of the dried or lyophilized mobile conjugate pad or membrane 15. Rather the concept of the application of a liquid sample 10 directly to the dried or lyophilized mobile conjugate pad or membrane 15, located on the opposite side and upstream of the sample receiving pad or membrane 13, enabling a more complete mixture with the conjugate 22 and sample fluid 10.

Applying the present invention provides membrane strips and improved methods for the practice of chromatographic specific binding assay techniques. Detection membrane strip 12 is selected to have a sufficient pore size such that the conjugate 22 reagent may be comprised of latex, gold, silver, selenium, carbon, but are not limited to these elements. Sample 10 migrates by capillary action. Sample 10 size is determined by the capacity of the wick pad 14 and may be as much as 500 μl compared to 10 μl to 20 μl of effective sample 10 as constrained by one-step lateral flow assays in the prior art. Test samples 10 interact with the conjugate 22 to produce a near complete homogeneous mixture of conjugate 22 and sample 10. Thus each conjugate particle 22 contains a uniform number of captured analyte molecules, and further each conjugate particle 22 contains about the same number of captured analyte molecules as shown in FIG. 1.

By placing the conjugate pad or membrane 15 containing ligand bound to densely colored particles such as latex, gold, silver, selenium, carbon, and the like on a reverse or opposite side of the sample receiving membrane 13, but not in contact with the sample receiving pad or membrane 13; the analyte detection improves on the order of 2 to 10 fold over the conventional chromatographic specific binding assay techniques. In simplest practice as illustrated in FIG. 4 the test strip 44 is placed in test tube 40 containing approximately 110.mu.l to 500.mu.l of sample 10. When the sample 10 solution contacts the conjugate pad or membrane 15, particle conjugate 22 is rapidly expressed into the sample 10 where the test ligand has opportunity to react with said conjugate particles 22. As sample 10 migrates into the flow membrane, the ligand-particle conjugate is carried along flow path 46 where it is given opportunity to react with the capture ligand attached to the detection membrane 12. To better understand the Figs., it is noted that cassette 16 of FIGS. 1, 2, 5A and 5B can be the functional equivalent of test tube 40 of FIG. 4. In all embodiments cassette 16 and test tube 40 allow conjugate membrane 15 and receiving membrane 13 to be in liquid communication despite being on opposite sides of laminate 11.

The detection membrane strip 12 of this invention is characterized by a high capture efficiency, which is particularly advantageous in the use of the invention for diagnosis of pediatric and geriatric patients where the volume of sample 10 fluids obtainable from such patients may be limited.

This lateral flow assay platform is also suitable for analysis of samples 10 with heavy loads of particulate matter without the necessity of a prefilter. Particulate matter does not interfere with analyte determination at the location of the reaction site 12a, but instead accumulates at the interface of the sample application means and the chromatographic material. Nevertheless, prefilters may be used and fitted into sample application means for samples having especially heavy loads of particulate matter, for example, whole blood.

Figures 5A, 5B:
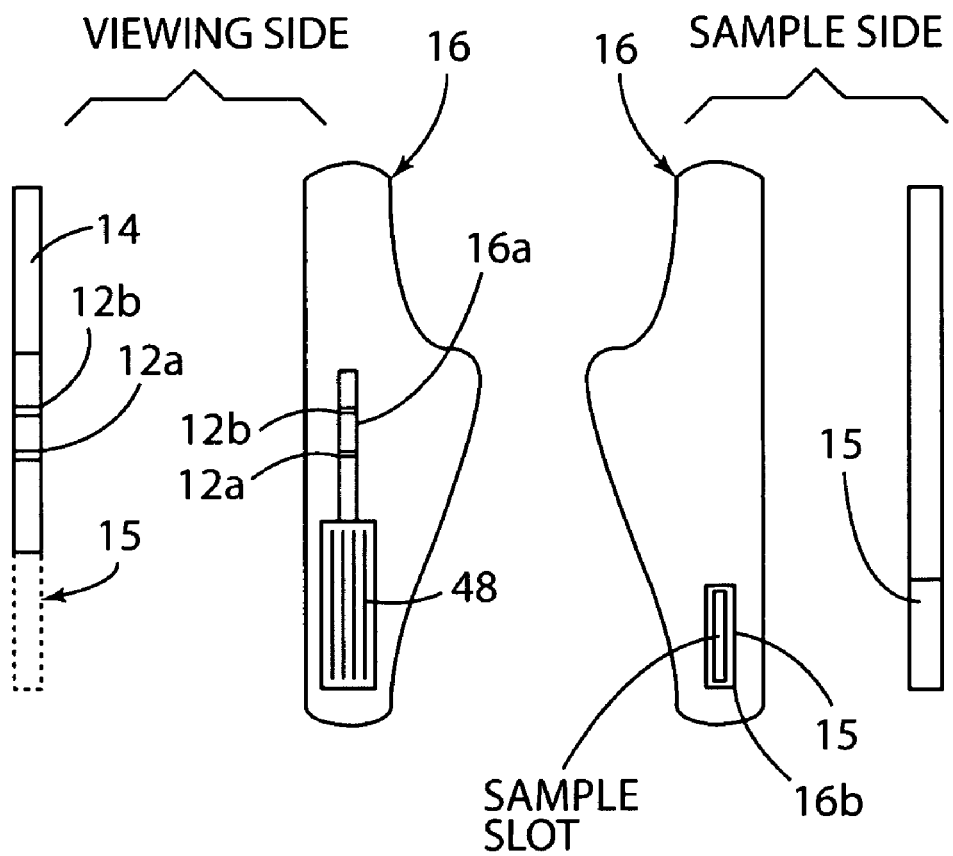
FIG. 5 is an expanded side view of a cassette holder in accordance with the objects' present invention.

FIG. 5 shows a diagram of an assembled strip holder (cassette 16). FIG. 5a shows the viewing side of cassette 16 and corresponding laminate 11 configuration. FIG. 5b shows a view of the cassette 16 having a sample receiving opening 16b and the corresponding view of laminate 11. This apparatus performs two functions, first the sample 10 and conjugate 22 mix to homogeneity, and second, the mixture flows through the detection membrane 12, for detection at the viewing window 16a. Cassette 16 or test tube 40 are critical to proper mixing of the conjugate and sample 10. This also is distinguishable over the one-step lateral flow assay in that cassette 16 or test tube 40 is required for the entire sample 10 to mix with the dried conjugate at conjugate pad or membrane 15.

Test Tube 40 Version of the Invention

One embodiment of the present invention allows the chromatographic test assay to be performed in a test tube 40 as shown in FIG. 4. In this case, sample 10 is added to tube 40 and detection strip 44 is inserted. The properties of the conjugate 22 are such that it immediately goes into solution upon contact with sample 10. Conjugate 22 and sample 10 come to homogeneity rapidly, and the mixture then flows to the sample receiving pad or membrane 13 and analysis of the detection window 16a is performed.

Cassette 16 Version of the Invention

Figure 6:
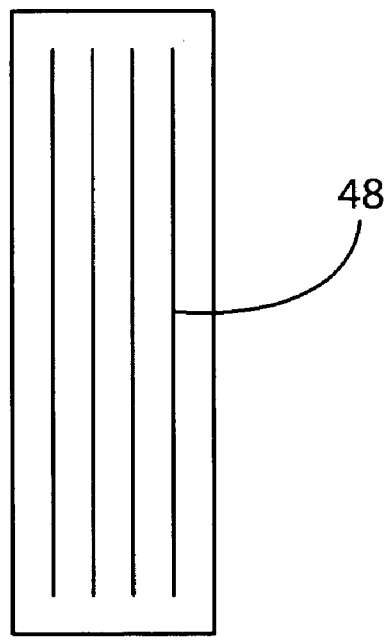
FIG. 6 is an example of a cassette configuration of the present invention adding detail showing homogeneous mixing.

In another embodiment a sample 10 is applied on the reverse side of detection strip 12 via an opening 16b in the strip cassette 16. As sample 10 mixes the conjugate 22 in the conjugate pad or membrane 15, it quickly collects in the bottom of cassette 16. Further, cassette 16 may contain plastic rods, chambers, or channels which further allow for a homogeneous mixing of the conjugate 22 and sample 10 as shown in FIG. 6. The conjugate-sample mixture may be moved to the detection membrane strip 12 via channels or ridges 48 located in the cassette as shown in FIG. 6.

In one embodiment of the present invention, the assay strip 34 has detecting antibodies. The immuno-reactive protein may be a ligand to which antibodies contained in a positive sample 10 reacts with such as HIV, HTLV, TB, and the like. Detection membrane strip 12 may be impregnated with anti-antibody to capture total, class and subclass immunoglobulins. In this case, the specific antibody in sample 10 reacts with ligand peptides (HIV, HTLV, TB, and the like) coated onto the surface of the particles 22.

In another embodiment of this invention, device 34 may have antigen on both the conjugate pad or membrane 15 and detection membrane strip 12 surfaces to which specific antibody may then be able to react with separate binding domains on the antibody. If detection membrane strip 12 is detecting antigen as the analyte, the membrane 12 surface may be impregnated with antibody or ligand reactive with the antigen. Typical antigen capture examples are specific antigen peptides, HIV p24 antigen, Hepatitis B surface antigen, cardiac markers, bacterial cells and the like and are known in the art. A colored line formed in this area may indicate detectable levels of analyte. A control zone, which indicates to the user whether or not the test was successfully run may also be included and illustrated in figures. In this example, the control in region 12b reacts with the conjugate. Often for human samples the control line is an antibody fragment, such as Fragment antigen binding (FAB)'2 goat anti human IgG (H&L) from Jackson Immunoresearch or KPL. (FAB)'2 has two antigen-binding arms that remain linked. Using FAB material prevents the binding of the protein A coated gold particles 22, and indicates the addition of human sample 10 (containing antibody). If buffer alone is added to the test strip, no control line develops resulting in an invalid assay. A colored conjugate to which purified proteins, haptens, or antibody to human immunoglobulins is chemically attached. The dried or lyophilized conjugate 22 on the conjugate pad or conjugate membrane 15 is mixed with special solubilizing and releasing compounds in a buffer; facilitating any interaction with the sample 10 bio-fluid.

While the invention has been described in conjunction with specific embodiments, it is evident that many alternatives, modifications and variations will be apparent to those skilled in the art in light of the foregoing description. Accordingly, the present invention attempts to embrace all such alternatives, modifications and variations that fall within the spirit and scope of the appended claims.

The invention claimed is:

1. A chromatographic specific binding assay strip device comprising a laminate strip having a first side and an opposite second side, said laminate strip comprising:
   (a) a fibrous conjugate pad comprising a colloidal labeled immunological binding reagent, said fibrous conjugate pad is disposed on said first side of said laminate; said fibrous conjugate pad has a first end and a second end, and is adapted to receiving a liquid sample applied directly thereto;
   (b) a fibrous sample receiving pad disposed on said second side of the laminate; said fibrous sample receiving pad is in liquid communication with at least the first or second end of the fibrous conjugate pad;
   (c) a fibrous reservoir pad disposed on the second side of said laminate and
   (d) a fibrous detection pad disposed between said fibrous sample pad and said fibrous reservoir pad;
   wherein said sample receiving pad, fibrous detection pad and fibrous reservoir pad are in capillary liquid communication facilitating a unidirectional migration of liquid from the sample receiving pad through the detection pad into the reservoir pad.

2. The device of claim 1 further comprising a cassette wherein said assay strip is encased inside said cassette; said cassette further comprising a sample slot on one side of the cassette for receiving the liquid sample onto the conjugate pad of said assay strip.

3. The device of claim 1 wherein the sample receiving pad and conjugate pad further comprise blocking agents including bovine serum albumin and detergent.

4. The device of claim 1, wherein said detection pad is impregnated with antibody to capture total, class and subclass immunoglobulins.

5. The device of claim 2, wherein said cassette contains ridges or further includes channels on the opposite side of said sample slot.

6. A kit comprising the device of claim 1 and a buffered diluent.

7. A kit comprising the device of claim 2 and a buffered diluent.

8. A method of detecting the presence or absence of analyte or ligand in a liquid sample comprising the steps of:
   applying the sample liquid to the fibrous conjugate pad of claim 1;
   allowing the sample to form a mixture comprising analyte-colloidal labeled immunological reagent complexes;
   allowing the mixture to flow by capillary action from the conjugate pad to the sample receiving pad and the detection pad;
   detecting the presence or absence of the complexes in the detection pad and relating the presence or absence of the complexes to the presence or absence of the analyte in the test sample.

9. The method of claim 8 wherein the analyte or ligand is selected from the group consisting of proteins, modified proteins, hormones, peptides, drugs, carbohydrates, haptens, and chemicals.

10. The method of claim 8, wherein the liquid sample is selected from the group consisting of a bio-fluid, plant extracts, environmental samples, tissue samples and enrichment broths.

11. The method of claim 8, wherein the sample is prefiltered to remove heavy loads of a particulate matter.

12. The method of claim 8, wherein the analyte is selected from the group consisting of an infectious disease marker, a pregnancy marker, a microbe, an ovulation marker, a cancer marker, an autoimmunity marker, a cardiac marker, a bio-warfare agent, an allergy marker, a drug of abuse and an environmental monitoring marker.

13. The method of claim 10, wherein the bio-fluid is selected from the group consisting of tissue extracts, blood, serum, plasma, tears, perspiration, urine, and saliva.

* * * * *